(12) United States Patent
Jackson (10) Patent No.: US 10,004,541 B1
(45) Date of Patent: Jun. 26, 2018

(54) CLOSURE FOR OPEN-HEADED MEDICAL IMPLANT

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days. days.

(21) Appl. No.: 15/883,993

(22) Filed: Jan. 30, 2018

Related U.S. Application Data

(63) Continuation of application No. 15/144,915, filed on May 3, 2016, now Pat. No. 9,907,577, which is a continuation of application No. 14/509,496, filed on Oct. 8, 2014, which is a continuation of application No. 13/694,970, filed on Jan. 23, 2013, which is a continuation of application No. 10/142,614, filed on May 9, 2002, now Pat. No. 8,377,100, which is a continuation-in-part of application No. 10/014,434, filed on Nov. 9, 2001, now Pat. No. 6,726,687, which is a continuation-in-part of application No. 09/732,528, filed on Dec. 7, 2000, now Pat. No. 6,454,772.

(51) Int. Cl.
*A61B 17/70* (2006.01)
*A61B 17/68* (2006.01)
*A61B 90/00* (2016.01)

(52) U.S. Cl.
CPC ........ *A61B 17/7032* (2013.01); *A61B 17/685* (2013.01); *A61B 17/686* (2013.01); *A61B 17/7082* (2013.01); *A61B 17/7091* (2013.01); *A61B 2090/037* (2016.02)

(58) Field of Classification Search
CPC . A61B 17/685; A61B 17/686; A61B 17/7091; A61B 17/7032; A61B 2019/307
See application file for complete search history.

(56) References Cited

U.S. PATENT DOCUMENTS

| | | |
|---|---|---|
| 2,005,348 A | 6/1935 | Michell |
| 2,833,325 A | 5/1958 | Laisy |
| 4,600,225 A | 7/1986 | Blose |
| 5,067,955 A | 11/1991 | Cotrel |
| 5,092,635 A | 3/1992 | DeLange et al. |
| 5,234,430 A | 8/1993 | Huebner |
| 5,334,203 A | 8/1994 | Wagner |
| 5,605,458 A | 2/1997 | Bailey et al. |
| 5,607,304 A | 3/1997 | Bailey et al. |
| 5,672,176 A | 9/1997 | Biedermann et al. |
| 5,797,911 A | 8/1998 | Sherman et al. |

(Continued)

FOREIGN PATENT DOCUMENTS

WO    WO 95/13755    5/1995

OTHER PUBLICATIONS

European Search Report, EP14189707.4, dated Feb. 25, 2015.

*Primary Examiner* — Julian W Woo
(74) *Attorney, Agent, or Firm* — Polsinelli PC (57) ABSTRACT

A closure for an open headed medical implant, such as a bone screw. The closure having a cylindrical body having an axis of rotation and also having a radially outer surface with a thread or other guide and advancement structure thereon. The body having a plurality of apertures that open onto a top surface of the body and that are parallel to but spaced from the axis of rotation. The closure also has a break-off head centrally attached by a neck to the top surface of the body.

10 Claims, 5 Drawing Sheets

(56) References Cited

U.S. PATENT DOCUMENTS

| | | |
|---|---|---|
| 6,006,930 A | 12/1999 | Dreyer et al. |
| 6,010,502 A | 1/2000 | Bagby |
| 6,063,090 A | 5/2000 | Schlapfer |
| 6,077,262 A | 6/2000 | Schlapfer et al. |
| 6,077,267 A | 6/2000 | Huene |
| 6,254,146 B1 | 7/2001 | Church |
| 6,296,642 B1 | 10/2001 | Morrison et al. |
| 6,412,831 B1 | 7/2002 | Noel et al. |
| 6,554,834 B1 | 4/2003 | Crozet et al. |
| 9,636,146 B2 | 5/2017 | Jackson et al. |
| 9,717,533 B2 | 8/2017 | Jackson et al. |
| 9,743,957 B2 | 8/2017 | Jackson |
| 9,795,415 B2 * | 10/2017 | Bono ................. A61B 17/7035 |
| 9,907,577 B2 * | 3/2018 | Jackson ............. A61B 17/7032 |
| 2014/0214097 A1 | 7/2014 | Jackson et al. |
| 2015/0119942 A1 | 4/2015 | Jackson et al. |
| 2015/0148846 A1 | 5/2015 | Jackson |
| 2015/0164558 A1 | 6/2015 | Jackson et al. |
| 2016/0038188 A1 | 2/2016 | Jackson et al. |
| 2016/0242818 A1 | 8/2016 | Jackson |
| 2017/0189073 A1 | 7/2017 | Jackson et al. |
| 2017/0333083 A1 | 11/2017 | Jackson et al. |
| 2017/0340363 A1 | 11/2017 | Jackson |
| 2017/0354441 A1 | 12/2017 | Jackson et al. |
| 2017/0354443 A1 | 12/2017 | Jackson |

\* cited by examiner

CLOSURE FOR OPEN-HEADED MEDICAL IMPLANT

CROSS REFERENCE TO RELATED APPLICATIONS

The present application is a continuation of U.S. application Ser. No. 15/144,915, filed May 3, 2016, now U.S. Pat. No. 9,907,577, which is a continuation of U.S. application Ser. No. 14/509,496 filed Oct. 8, 2014, now abandoned, which is a continuation of U.S. application Ser. No. 13/694,970, filed Jan. 23, 2013, now abandoned, which is a continuation of U.S. application Ser. No. 10/142,614, filed May 9, 2002, now U.S. Pat. No. 8,377,100, which is a continuation-in-part of U.S. application Ser. No. 10/014,434 filed Nov. 9, 2001, now U.S. Pat. No. 6,726,687, which is a continuation-in-part of U.S. application Ser. No. 09/732,528, filed Dec. 7, 2000, now U.S. Pat. No. 6,454,772, each of which is fully incorporated by reference herein for all purposes.

BACKGROUND OF THE INVENTION

The present invention is directed to an open headed medical implant and, in particular, to a closure for closing the head of an open headed bone screw, hook or the like.

Bone screws are used especially in spinal surgery to support and position various implants needed to repair a spine that has suffered injury, illness or genetic defect. Bone screws of this type are screwed into the vertebrae of the spine and have a head that projects outside the bone which receives other implants, such as rods, that extend along the spine. Bone screws are of two general types which are either open headed or closed headed. Hooks and certain other implants also sometimes have open heads. The present application is directed to open headed bone screws and related implants such as hooks and the like that have such an open head to receive another implant.

In open headed bone screws and related implants, the head includes two upright arms that form a channel therebetween. The channel is sized to receive a rod or the like and is open to make it easier to place the rod in the head. The rod must then be tightly held or locked in the head to prevent relative movement between implants after the surgery. To hold the rod in the head, plugs have been used that are screwed into threads on the interior surfaces of the arms.

The present invention is directed especially to improvements in such plugs or closures that make them easier to insert in the head, that better ensure that the plug effectively secures the rod so that the rod does not later slip, that allow the plugs to be easily removed should the overall implant system require rearrangement and which provide a comparatively low profile, so as reduce trauma and irritation to the surrounding tissues of the patient.

SUMMARY OF THE INVENTION

A closure is provided for an open headed implant, especially a bone screw or hook for use in spinal surgery. The closure has a cylindrical shaped body with an axis of rotation. The body has a radially outer surface that has a thread or other guide and advancement structure thereon that is sized and shaped to be received in mating threads or structure on interior surfaces of arms of the implant head. The closure is operably rotated and advanced into the head of the implant to capture a rod or other part of an overall spinal support system. The closure captures and locks such a rod in position relative to the implant to prevent rotation or axial movement between the joined parts.

The closure body has a top surface and a bottom surface with a plurality of cylindrical bores extending parallel to the axis of rotation into the body from the top surface or other removal apertures. The bores or apertures are positioned in spaced relationship to one another and to the axis of rotation. The bores or apertures are sized and shaped to cooperatively mate with posts on a tool to allow removal of the closure from the implant after insertion, should such be necessary.

The closure also includes a break-off head centrally mounted by a neck on the top surface of the body. The break-off head is adapted to receive a socket tool and be rotated thereby during installation. The break-off head is also designed to break from the body at a torque limiting or break-off region or location which is preferably whereat the neck intersects with the top surface of the body, when a preselected torque is applied to the break-off head. When the break-off head is broken away, the bores or apertures become exposed and are mateable with a removal tool should it become necessary to remove the closure.

In a second embodiment the body includes a central threaded bore that receives a set screw. The body is then used for capture of a rod or the like and the set screw is used to lock the rod or the like in position relative to the implant.

In a third embodiment, a body includes both a break-off head and a central threaded bore that is covered by the break-off head until the head breaks away, after which the threaded bore is exposed at the top surface of the body to receive a set screw.

OBJECTS AND ADVANTAGES OF THE INVENTION

Therefore, the objects of the present invention are: to provide a closure for an open ended implant that provides a plurality of spaced removal apertures that are offset from an axis of rotation of the closure and that cooperate with a tool to allow removal of the closure; to provide such an implant having a closure with a break off head for mating with an insertion tool for inserting the closure into the implant; to provide such an implant wherein the removal apertures are not accessible for effective access, when the closure is in the implant until the break-off head is broken away; to provide such an implant that strongly grips a rod or the like received in the implant and that provides a relatively low profile; and to provide such an implant and closure therefor that is relatively easy to use, comparatively easy to produce and is especially well suited for the intended use thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a medical implant in accordance with the present invention. The implant 1 includes a bone screw 5, a closure 6 for the bone screw 5 and a rod 7. The implant 1 is received in a vertebrae 9, typically in conjunction with other implants that are not shown. The closure 6 also functions in conjunction with other open-headed implants, such as hooks and the like.

The bone screw 5 includes a shank 12 and a head 13. The shank 12 is threaded with a coarse helically wound flighting-like thread 16 that is threaded into the vertebrae 9, so as to secure and support the bone screw 5 and allow the head 13 to extend from the vertebrae 9.

The bone screw head 13 includes a base 20 with a pair of upstanding spaced arms 21 and 22 on opposite sides of the base 20 forming a generally U-shaped configuration, when viewed from the side, and defining a channel 23 therebetween. The channel 23 is sized and shaped to receive the rod 7.

The arms 21 and 22 each include an interior surface 26 and 27 respectively. The interior surfaces 26 and 27 have a guide and advancement structure which in the illustrated embodiment is a partial helical wound thread 29 on each. While the illustrated thread 29 is a conventional V-shaped thread, the purpose of this thread is to engage similar threads on the closure 6 to guide the closure 6 relative to the bone screw 5, as discussed below, and to provide for biased advancement of the closure 6 along the central axis A thereof relative to the bone screw 5 upon rotation of the closure 6. It is foreseen that other structures including other types of threads, such as buttress and reverse angle threads, and non threads, such as helical wound flanges or the like having interlocking surfaces, could be alternatively used for this purpose. Therefore, the illustrated internal partial or discontinuous threads on the bone screw arms 21 and 22 along with the mating thread on the closure 5 provide guide and advancement structure that operably positions and advances the closure 6 relative to the bone screw 5 during installation. The threaded surfaces 26 and 27 are spaced and not connected so as to present only a partial threadform which each face one another and cooperate with the closure 6, as is noted below. In the illustrated embodiment, the threaded surfaces 26 and 27 extend from a top 30 of the bone screw 5 only partially down the arms 21 and 22.

Figures 1, 2, 3:
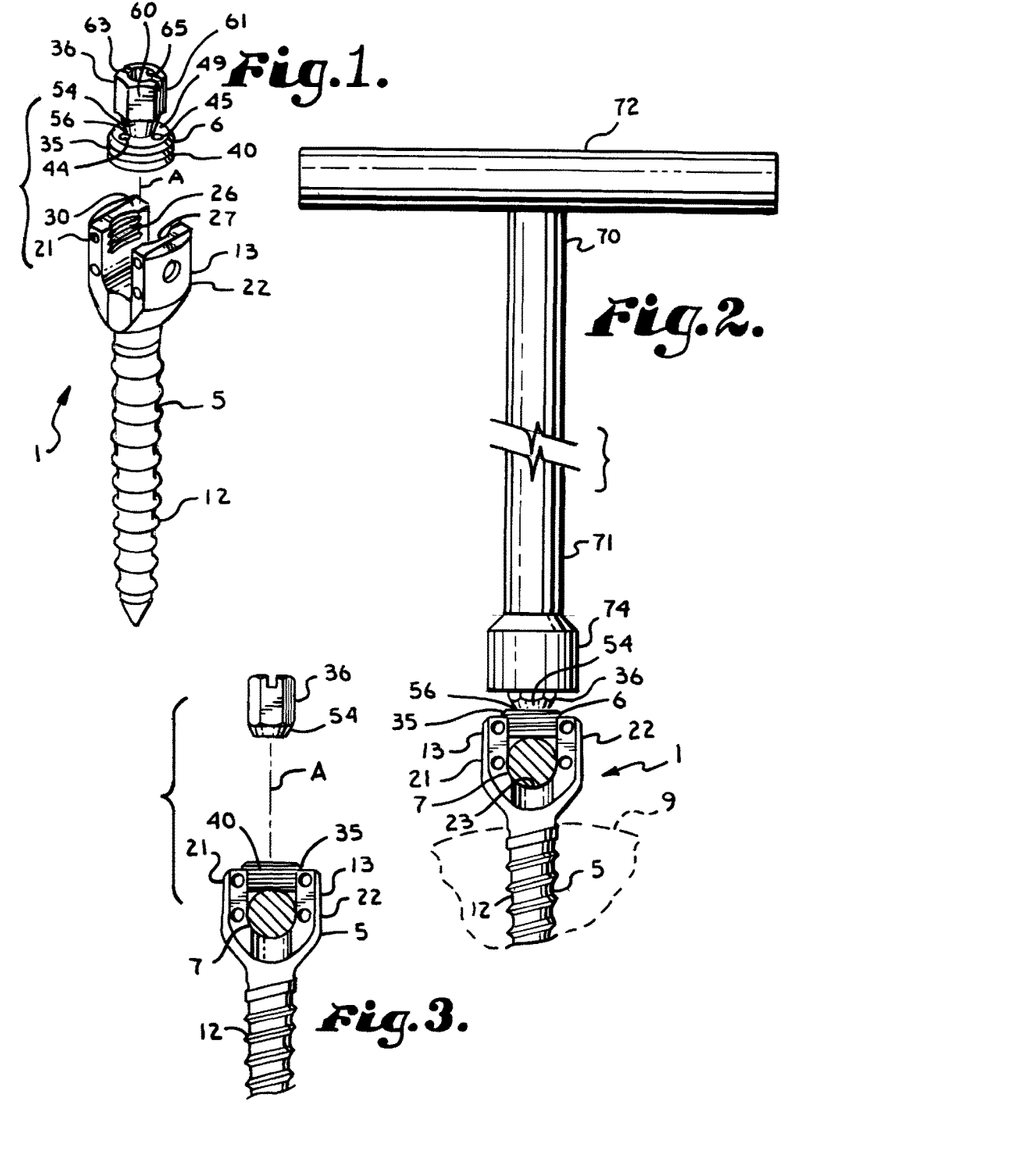
FIG. 1 is an exploded perspective view of a bone screw type implant and closure in accordance with the present invention prior to insertion of the closure into a head of the bone screw.
FIG. 2 is a fragmentary side elevational view of the bone screw with a rod and the closure received therein and with a tool being utilized to insert the closure and provide torque to the break-off head of the closure and further with the bone screw shown embedded in a bone that is indicated by phantom lines.
FIG. 3 is a fragmentary and exploded side elevational view of the bone screw, rod and closure with the break-off head of the closure being shown broken therefrom.

The closure 6 includes a body 35 and a torque limiting break-off head 36. The closure body 35 is generally cylindrical in shape and has a radially outward external surface 40 that extends 360° about an axis of rotation indicated by the reference letter "A". In the present embodiment, the surface 40 has a portion of the mating guide and advancement structure thereon which in the illustrated embodiment is a thread 41 that mates with the partial thread 29 on the bone screw 5 and biases the closure 6 forward due to interaction of the threads 29 and 41 upon clockwise rotation of the closure 6. As noted before, this function can be provided by alternative types of threads or other non threaded structures such as a helically wound flange that slidably mates with a similar structure on the bone screw 5. In the illustrated embodiment the threaded surface 40 has a threadform located thereon that entirely encircles the outer surface 40 of the body 35 and extends entirely from top to bottom. The surface 40 is provided with a thread 41 that is sized, shaped and configured to threadably mate with the threaded surfaces 26 and 27 of the arms 21 and 22, so that the closure body 35 may be threaded into the bone screw head 13, as is shown in FIG. 2.

The closure body 35 also includes at least one removal aperture and in the illustrated embodiment such an aperture is provided by three bores 44, 45 and 46 that are aligned to be parallel with the axis of rotation. The bores 44, 45 and 46 are spaced both from the axis of rotation A and from a periphery 48 of a top 49 of the body. The bores 44, 45 and 46 extend from the body top 49 to a bottom surface 50 of the body 35 in the illustrated embodiment. Preferably the bores 44, 45 and 46 are equally spaced from one another and are approximately equally radially spaced outward from the axis of rotation A. In the illustrated embodiment, the bores 44, 45 and 46 are spaced at approximately 120° from one another.

While three cylindrical bores are shown and function as the removal aperture in the illustrated embodiment, it is foreseen that various numbers of openings could be equivalently used and/or such apertures may be of various shapes, such as round, square or kidney bean in cross section, and may be pass through from top 49 to bottom surface 50 of the closure 6 or may just pass through the top 49 thereof and extend partially therethrough.

The break-off head 36 includes a neck 54 that joins with the body top 49 at a torque limiting region or break-off location 56. Preferably the break-off location 56 is generally coplanar with the body top 49, so the break-off location 56 is clean and low profile after such breakoff. The break-off location 56 is normally determined by the location whereat the neck 54 is smallest in cross-section or the location 56 can be triggered by an external groove and other devices known for this purpose. The neck 54 also converges somewhat from the remainder of the break-off head 36 to the break-off location 56.

The break-off head 36 includes a number of facets or panels 60 which are aligned to be parallel to the axis of rotation A and which are joined together to form a polyhedral shaped surface 61 typically associated with a structure to be received in a socket-type tool. The combined surface 61 of the facets 60 forms such a polyhedral shape. A top surface 63 of the break-off head 36 has axially located therein a non-threaded bore 65 for operably receiving a tool during implantation. The bottom surface 50 of the body 35 includes a conical shaped and axially aligned point 67 for engaging and preferably biting into the rod 7, so as to provide an improved grip on the rod to prevent rotation or axial movement thereof relative to the bone screw 5. It is foreseen that the bottom surface 50 may be flat or otherwise shaped and may include other structure to increase frictional engagement between the closure 6 and the rod 7, such as: knurling; a ring with a sharp lower edge, especially when used in conjunction with and surrounding the point 67; or the like.

A tool 70 is illustrated in FIG. 2 for cooperatively inserting the closure 6 into the bone screw head 13. The tool 70 has an elongate shank 71 with a handle 72 sized and shaped to allow a user to rotate the tool 70 clockwise about the axis of rotation A associated with the closure 6. The tool 70 also has a socket type head 74 opposite the handle 72 that is sized and shaped to snugly receive the outer surface 61 of the break off head 36 as is shown in FIG. 2.

During assembly, the rod 7, which is elongate and generally circular in cross-section, is placed within the bone screw channel 23 and the closure 6 is then threaded into the bone screw head 13. The tool 70 is used to rotate the closure 6 until it engages the rod 7 and urges the rod 7 to seat tightly and snugly on the bone screw head base 20 at the bottom of the channel 23. The point 67 engages and digs into the rod 7. As additional torque is applied to the tool 70, a preselected torque is eventually reached (for example 90 inch pounds) whereat the break-off head 36 breaks from the closure body 35 at the break-off location 56 and separates therefrom, such as is shown in FIG. 3.

Figures 4, 5, 6, 7, 8:
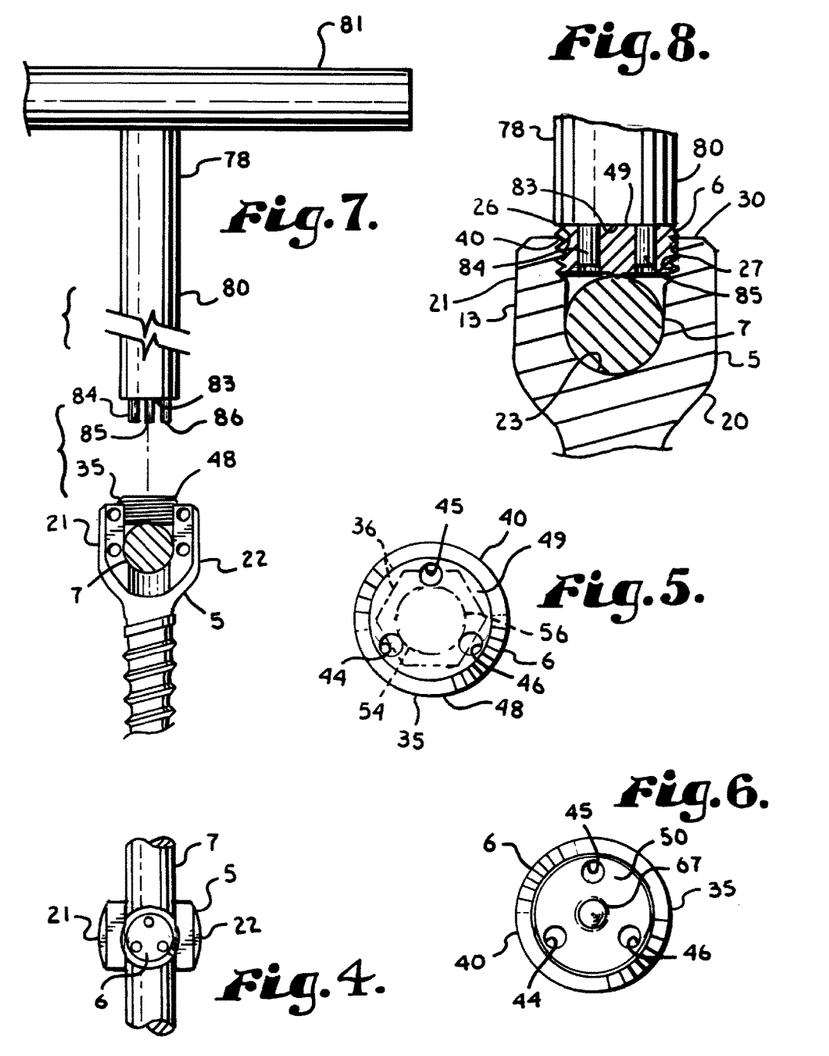
FIG. 4 is a fragmentary top plan view of the bone screw, rod and closure with the break-off head removed.
FIG. 5 is a top plan view of the closure with the break-off head broken therefrom, but shown in phantom.
FIG. 6 is a bottom plan view of the closure.
FIG. 7 is an exploded and fragmentary side elevational view of the bone screw, rod and closure showing a removal tool positioned above the closure.
FIG. 8 is a fragmentary and enlarged view of the bone screw, rod and closure shown in FIG. 7 with the removal tool inserted into the closure and with portions of the bone screw and closure broken away to show detail thereof.
Figure 9:
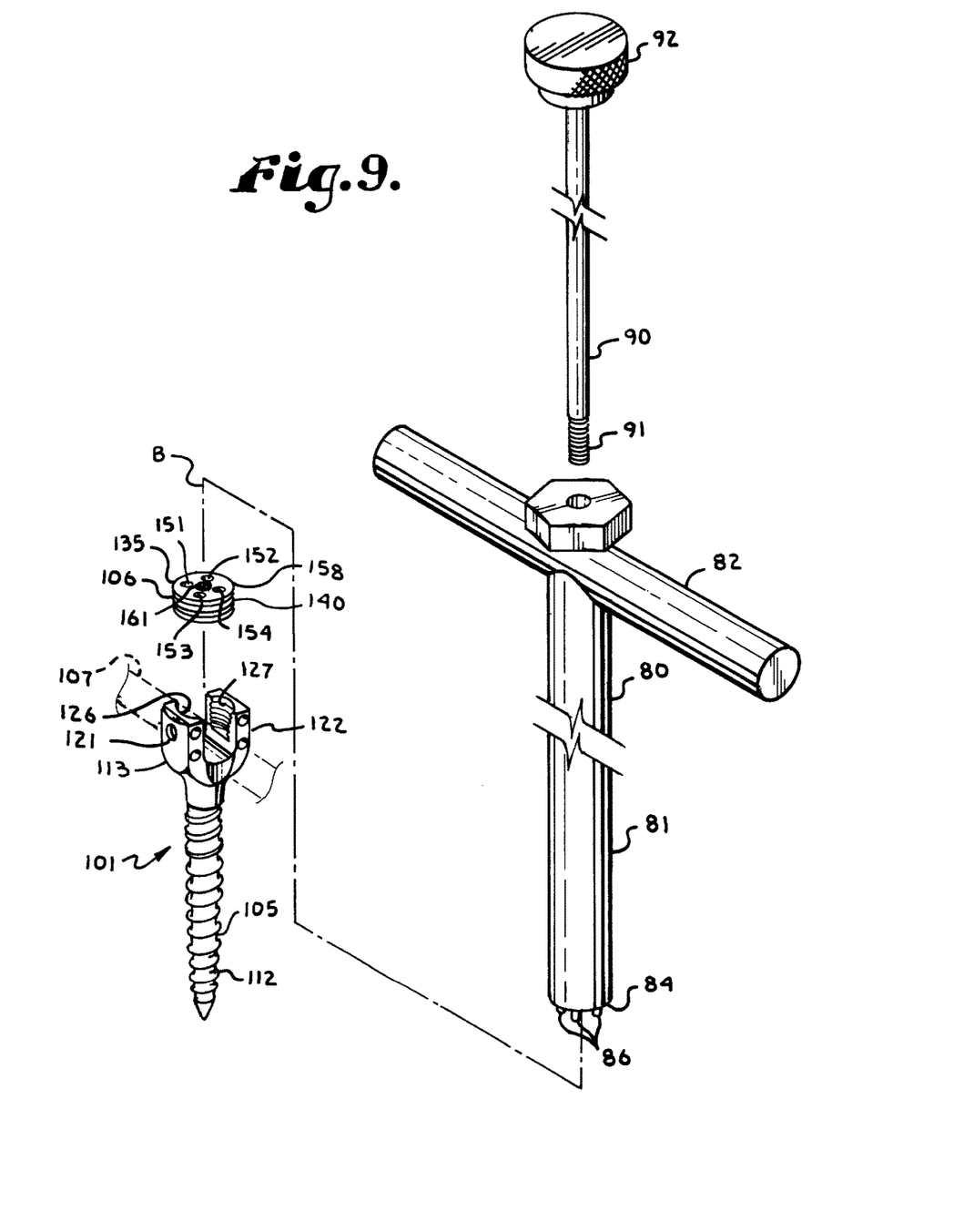
FIG. 9 is an exploded perspective view of a modified bone screw and closure in accordance with the present invention, also showing a rod received in a head of the bone screw in phantom lines and a tool for use in inserting the closure into and removing the closure from the head of the bone screw.

FIGS. 3 and 4 illustrate the closure 6 operably positioned within the bone screw head 13. FIG. 5 illustrates the closure 6 with the break-off head 36 removed, but shown in phantom to illustrate the position of the break-off head 36 relative to the bores 44, 45 and 46.

In certain circumstances, it is necessary to remove the closure 6 to readjust the position of the rod 7 or to make some other change in the implant 1 configuration. As mentioned before, the implant 1 is typically a part of an overall system and is normally used to provide support to damaged, injured or missing vertebra of the spinal column. When it is necessary to readjust the overall system, the closure 6 is removed by utilization of the second tool 78. The tool 78 includes a shank 80 that has an axis of rotation during use that is coaxial with the axis of rotation A of the closure 6. The shank 80 is attached at one end to a handle 81 to provide a grasp and a means of turning the tool 78 by a user. Opposite the handle 81, the shank 80 has a flat surface 83 from which three pegs or posts 84, 85 and 86 project.

The posts 84, 85 and 86 are parallel to the axis of rotation of the tool 78 and are sized, shaped and positioned so as to be snugly receivable in the closure bores 44, 45 and 46, subsequent to removal of the break-off head 36. The tool 78 is shown in position above the closure body 35 in FIG. 7 just prior to insertion of the posts 84, 85 and 86 into respective bores 44, 45 and 46. The tool 78 is shown positioned with the posts 84, 85 and 86 in the respective bores 44, 45 and 46 in FIG. 8. The purpose of the tool 70 is to allow a user to rotate the closure body 35 counter-clockwise and remove the body 35 from the bone screw head 13 after the closure 6 has been seated therein. In this way the channel 23 can be reopened and the rod 7 removed or repositioned relative to the bone screw head 13.

While the non-axially located bores 44, 45 and 46 of the present embodiment are located between the break-off head neck 54 and the periphery 48, it is foreseen that one or more non-axial bores of this type could partially or entirely intersect with the neck 54 so as to become fully open or exposed at the closure top surface 49 only when a break-off head associated with such a neck breaks from the closure body.

Illustrated in FIGS. 9 to 13 is second embodiment or first modified embodiment of an implant in accordance with the present invention that is generally identified by the reference numeral 101. The implant 101 includes a bone screw 105, a closure 106, a rod 107 and a set screw 108.

The bone screw 105 except for the closure is essentially the same as the bone screw 5 and, therefore, will not be described in detail. Reference is made to the description of bone screw 5 for additional detail. The bone screw 105 has a shank 112 and a head 113. Upright arms 121 and 122 of the head 113 have inner or interior facing and threaded surfaces 126 and 127.

The rod 107 is elongate and has a generally circular cross section for being received in the head 113 beneath the closure 106.

Figure 10:
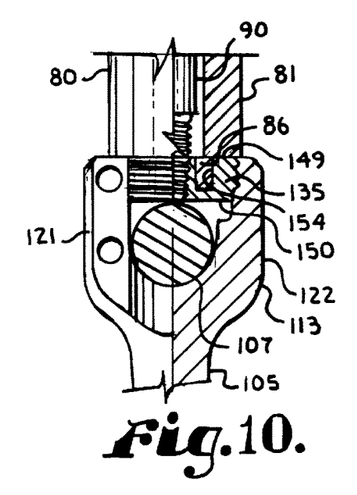
FIG. 10 is a side elevational view of the bone screw, rod, closure and tool of the second embodiment of the invention with portions broken away to show internal detail thereof.
Figure 11:
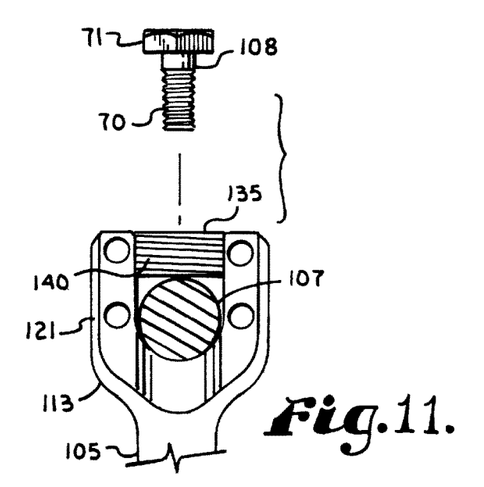
FIG. 11 is a fragmentary side elevational view of the bone screw, rod and closure also showing a set screw that is positioned to be received in the closure.
Figure 12:
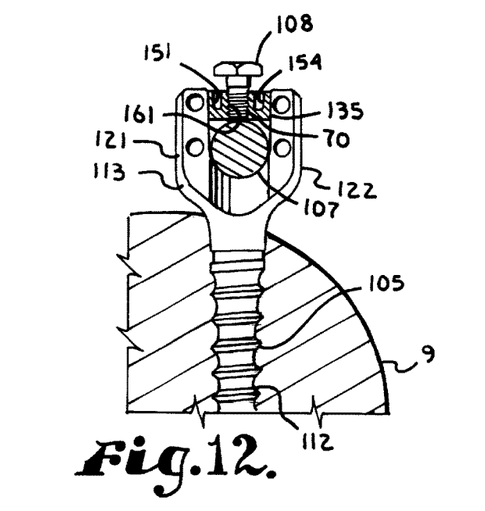
FIG. 12 is a fragmentary side elevational view showing the bone screw, rod, closure and closure set screw positioned in a vertebrae that is shown in cross-section.
Figure 13:
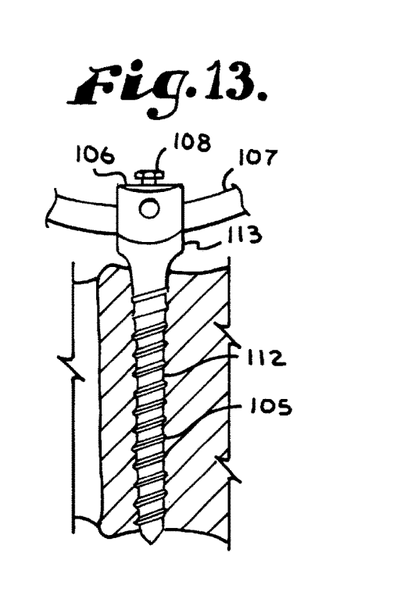
FIG. 13 is a front elevational view of the bone screw, rod and closure shown mounted in a vertebrae that is shown in cross-section.

The closure 106 is similar in some respects to the closure 6, but is installed in a different manner. In particular, the closure 106 has a generally cylindrical shaped body 135 that has a threaded radially outward surface 140 that has a thread thereon that is sized, shaped and positioned to threadedly mate with threads of the arm threaded surfaces 126 and 127, as seen in FIG. 10. The thread can be a conventional V-thread, a buttress thread, a reverse angle thread or other threads related to reverse angle threads in that they exert forces to draw or pull the arms 121 and 122 toward one another rather than cause them to splay or open at the top.

The closure 106 is similar in some respects to the closure 6, but is installed in a different manner. In particular, the closure 106 has a generally cylindrical shaped body 135 that has a threaded radially outward surface 140 that has a thread thereon that is sized, shaped and positioned to threadedly mate with threads of the arm threaded surfaces 126 and 127, as seen in FIG. 10. The thread can be a conventional V-thread, a buttress thread, a reverse angle thread or other threads related to reverse angle threads in that they exert forces to draw or pull the arms 121 and 122 toward one another rather than cause them to splay or open at the top.

The body 135 also has a top surface 149 and a bottom surface 150. Positioned to extend downwardly into the body 135 form the top surface 149 are four equally spaced bores 151, 152, 153 and 154 that do not extend entirely through the body 135 from top to bottom. The bores 151, 152, 153 and 154 are spaced form and positioned between both a central axis B and a periphery 158 of the body top surface 149. Each bore 151, 152, 153 and 154 is positioned at approximately 90° relative to adjacent bores 151, 152, 153 and 154.

Located axially and centrally in the body 135 is a threaded bore 161. The threaded bore 161 extends between the top surface 149 and bottom surface 150.

The set screw 108 has a threaded shaft 170 sized and shaped to be threadably received in the body threaded bore 161. The set screw 170 has sufficient length to extend through and outward from the bottom surface 150. In the second embodiment the set screw 108 has a head 171 that is gripable by a tool for rotation and torquing.

A tool 180 is provided for installing and removing the closure 106 form the bone screw head 113. The tool 180 is T-shaped having a shank 181 with a handle 182 attached to one end and a generally flat surface 184 at an opposite end. The surface 184 has four pegs or posts 186 extending therefrom. The posts 186 extend form the surface 184 parallel to an axis of rotation of the tool 180 which is the same in use as the axis of rotation B of the closure. The posts 186 are aligned, sized and shaped to mate with the closure body bores 151, 152, 153 and 154.

The tool shank 170 also includes an axial bore extending therethrough and receiving a keeper rod 190. The rod 190 has a threaded tip 191 that is adapted to be received in the closure body bore 161 and a grasping head 192 at an opposite end.

In use the rod 107 is placed in the head 112 and the tool 180 is mated with the closure 106 in the manner shown in FIG. 10, so that the four posts 186 are located in respective bores 151, 152, 152 and 154 and the rod tip 191 is threaded into the threaded bore 161. The closure 106 is then mated with the head 112 and threaded thereon by mating of the surface 140 with the arm surfaces 126 and 127 until the closure 106 is snug in the bone screw head 113. Torque in a preselected amount is applied to the closure 106 to ensure it is tightly seated in the head 112. In some instances, the closure 106 may just be used to capture the rod 107 and the set screw 108 is used to lock the rod 107 in place. In particular, the tool 180 may be removed and the set screw 108 is then placed in the bore 161 and advanced against the rod 107. A preselected torque is applied to lock the rod 107 in a selected position in the head 112.

It is foreseen that the set screw 108 may be of other types than the one illustrated. That is the set screw could have a break-off head in which case the overall implant 101 would have a comparatively low profile associated with only the top of the bone screw.

For removal, the installation process is reversed. That is the tool 180 is utilized to rotate the closure 106 counter-clockwise rather than the clockwise direction used for inserting. Where a break off set screw is used, the set screw can be rotated with the body 135 of the closure 106 for removal.

Figure 14:
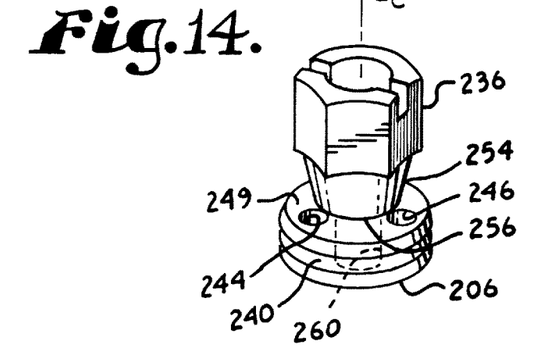
FIG. 14 is a side elevational view of a closure in accordance with a second modified embodiment of the present invention.
Figures 15, 16:
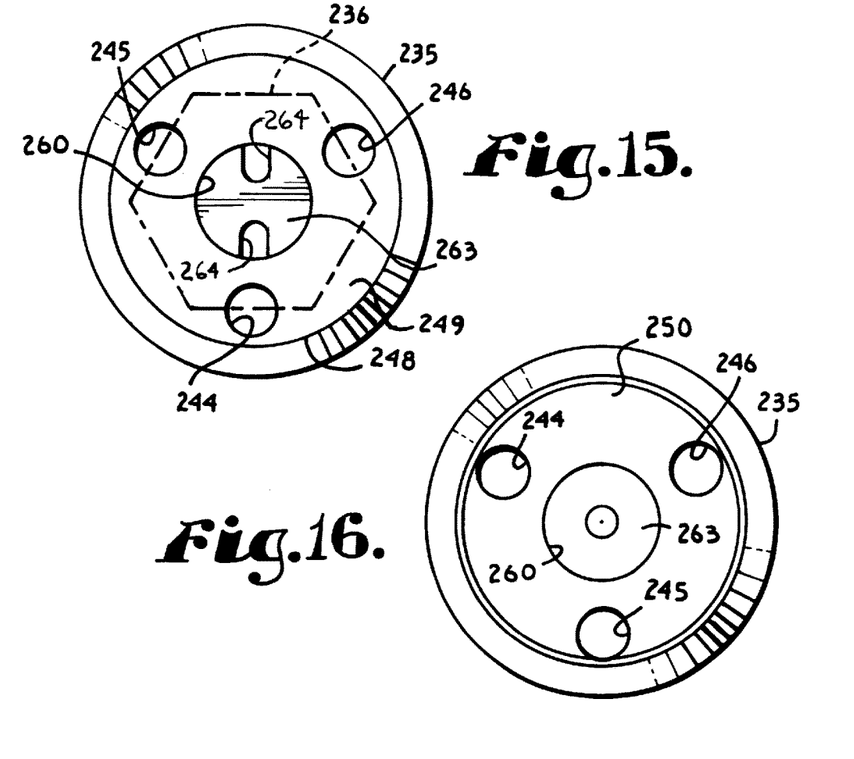
FIG. 15 is a top plan view of the closure of the second modified embodiment with a break-off head thereof broken away.
FIG. 16 is a bottom plan view of the closure of the second modified embodiment of the invention.

Illustrated in FIGS. 14, 15 and 16 is a third embodiment or second modified embodiment of a bone screw closure in accordance with the present invention and generally identified by the reference numeral 206.

The closure 206 is in many ways similar to the closure 6 and reference is made to the disclosure for the closure 6 for additional detail.

In particular the closure 206 has a generally cylindrically shaped body 235 that has a radially outer threaded surface 240. The closure 235 also has a break-off head 236 secured to a top or upper surface 249 of the body 235 by a neck 254 at a break-off location 256. Positioned between the neck 254 and a periphery 248 of the body upper surface 249 are three bores 244, 245 and 246 that extend parallel to a central axis of rotation identified by a reference numeral C.

The major difference between the present embodiment and the closure 6 shown in the first embodiment is that a body 235 thereof also includes a central or axial bore 260 extending from a bottom surface 250 upward through the body 235 to the level of an upper surface 249 of the body 235. The bore 260 is threaded and covered by the neck 254 until the break-off head 236 breaks form the body 235 during installation by application of torque, as was described in the first embodiment. The bore 260 is thereafter exposed upwardly or at the upper surface 249 and adapted to receive a set screw 263 of the type used in the second embodiment or alternatively a break-off type, as shown, set screw having removal slots 264. It is noted that the diameter of the neck 254 at the top surface 249 is larger than the diameter of the bore 260.

It is to be understood that while certain forms of the present invention have been illustrated and described herein, it is not to be limited to the specific forms or arrangement of parts described and shown.

What is claimed and desired to be secured by Letters Patent is as follows:

1. A medical implant comprising:
    a bone anchor head including a first upright arm and a second upright arm, the first upright arm having a first top surface and a first interior surface and the second upright arm having a second top surface and a second interior surface;
    a channel formed between the first upright arm and the second upright arm, the channel configured to receive a rod;
    a discontinuous helically wound thread extending along at least a portion of the first interior surface and the second interior surface;
    a multi-part closure having a closed ring body and a set screw, the closed ring body having a top body surface opposite a bottom body surface and an outer body surface, the set screw having a set screw outer surface;
    a plurality of spaced-apart tool mating structures formed within the top body surface and extending partially down into the closed ring body such that none of the plurality of spaced-apart tool mating structures intersect the bottom body surface;
    a threaded central bore extending between the top body surface and the bottom body surface;
    a continuous thread extending about the set screw outer surface;
    a closure helically wound thread extending about the outer body surface, the closure helically wound thread threadedly mating with the discontinuous helically wound thread such that the first arm and the second arm are not caused to splay or open at a top of the bone anchor head and the first top surface and the second top surface are not covered by the closed ring body during rotational advancement of the closed ring body within the channel; and a continuous bottom surface closing a lower portion of the set screw and configured to compress the rod into a locked position within the channel as the continuous thread of the set screw engages the threaded central bore, the locked position including an entirety of the set screw and the closed ring body positioned within the channel.

2. The medical implant of claim 1, wherein the plurality of spaced-apart tool mating structures are spaced from a central axis of the closed ring body and the outer body surface.

3. The medical implant of claim 1, wherein the plurality of spaced-apart tool mating structures are non-axially located with respect to each other.

4. The medical implant of claim 1, wherein the plurality of spaced-apart tool mating structures are shaped as bores.

5. The medical implant of claim 1, wherein the plurality of spaced-apart tool mating structures each include a square shaped opening.

6. The medical implant of claim 1, wherein the continuous bottom surface is flat.

7. The medical implant of claim 1, wherein no portion of the set screw or the closed ring body extends beyond the first top surface and the second top surface in the locked position.

8. The medical implant of claim 1, wherein the first upright arm and the second upright arm each include an exterior surface that is not covered by the closed ring body during the rotational advancement of the closed ring body within the channel.

9. The medical implant of claim 1, wherein the first top surface and the second top surface are not covered by the closed ring body in the locked position.

10. The medical implant of claim 1, wherein the closed ring body is advanced into the channel prior to the set screw being advanced.

* * * * *